United States Patent [19]

Garritano

[11] Patent Number: 4,468,953

[45] Date of Patent: Sep. 4, 1984

[54] VISCOSITY AND ELASTICITY OF A FLUID

[75] Inventor: Ronald F. Garritano, Flemington, N.J.

[73] Assignee: Rheometrics, Inc., Piscataway, N.J.

[21] Appl. No.: 400,683

[22] Filed: Jul. 22, 1982

[51] Int. Cl.³ ............................................. G01N 11/10
[52] U.S. Cl. ........................................................ 73/60
[58] Field of Search ...................................... 73/60, 59

[56] References Cited

U.S. PATENT DOCUMENTS

| | | | |
|---|---|---|---|
| 2,817,231 | 12/1957 | Barstow | 73/60 |
| 2,869,358 | 1/1959 | Heisig | 73/60 |
| 3,008,326 | 11/1961 | Martin | 73/60 |
| 3,128,620 | 4/1964 | Gupta | 73/60 |

Primary Examiner—S. Clement Swisher
Assistant Examiner—Joseph W. Roskos
Attorney, Agent, or Firm—Samuelson & Jacob

[57] ABSTRACT

Disclosed herein is a torsion tube apparatus for making on-line measurements of the viscosity and elasticity of a fluid. The apparatus includes a housing member, an outer cylinder having one end rotatably mounted with respect to the housing member, and a motor for rotating this outer cylinder. An elongated torsion tube is mounted concentrically within and spaced from the outer cylinder and has one end fixed to the housing member, with its other end freely disposed within the cylinder for torsional movement with respect to the fixed end. Therefore, an annular void is defined between the tube and cylinder. Fluid may be introduced through a conduit into the interior of the cylinder for flow therethrough and discharge therefrom, such that rotating motion of the fluid caused by rotation of the cylinder exerts a torsional force directly on the outer surface of the tube. A torsion indicating shaft extends concentrically through the tube, having its one end fixed to the free end of the tube. An indicator is fixed to the other end of the shaft. Accordingly, torsional force on the tube provides the sole source of rotative movement of the shaft that is detected by the indicator. The assembly provides a smooth axial path for the fluid which flows through the annular void between the outer cylinder and tube.

20 Claims, 3 Drawing Figures

VISCOSITY AND ELASTICITY OF A FLUID

BACKGROUND OF THE INVENTION

1. Field of the Invention

The present invention relates to an apparatus for measuring the viscosity and elasticity of a fluid such as a polymer melt. More particularly, the apparatus disclosed herein is particularly well suited for making such measurements in an "on-line" manner, during actual fluid processing. In accordance with the invention, such parameters are determined dynamically by measuring the characteristics of a continuously moving stream of fluid while such stream is being subjected to shear forces.

Changes in elasticity and viscosity are responsible for many of the variations in the processing and performance properties of polymer melts such as thermoplastics. In commercial use of such materials, the quality of the manufactured end product can usually be controlled successfully if such characteristics are known and controlled during the production process.

In the past, viscosity and elasticity of polymer melts were often measured "off-line". That is, a sample of the polymer melt was taken from the production apparatus, and then tested in a separate and often remote laboratory. However, because automated equipment can now make products from polymer melts at high speed, large numbers of products of poor quality, or products which do not conform to specifications, can be produced before the "off-line" results of viscosity and elasticity measurements are known.

Therefore, it is desirable to measure viscosity and elasticity of polymer melts, in an "on-line" procedure, during processing and production operations.

2. Description of the Prior Art

Various apparatus have been proposed which may be used to make measurements of the viscosity and elasticity of fluids such as polymer melts. Such apparatus include capillary or slit flow devices, and devices which measure rheological quantities by determining the shear characteristics of the polymer melt. The apparatus of the present invention is of the latter type, and operates dynamically on a continuous stream of fluid.

An example of shear measuring apparatus is the "Couette-Hatschek" rotating cylindrical viscometer, illustrated and described in *Plastics & Polymers*, February, 1973. That device includes concentric inner and outer cylinders. The inner cylinder is attached to a reduced diameter torsion cylinder which is, in turn, fixed to an upper ram mounted on the framework of the apparatus. A shaft is attached at one end to the inner cylinder and projects through the torsion cylinder out of the framework. A polymer melt is placed between the inner and outer cylinders and the outer cylinder is rotated to impart a shear force to the polymer material. The viscous drag of the material produces a torque, on the inner cylinder, which is interpreted as a shear stress.

The "Couette-Hatschek" viscometer, however, is prone to certain sources of error in measuring viscosity. One source of error is the requirement for an "end correction" to the cylinder length, which is necessitated by the viscous flow which takes place at locations other than in the annular gap between the cylinders. Complex secondary flows also occur at other locations in the fluid flow path and result in errors. Additionally, there are certain practical disadvantages to the "Couette-Hatschek" apparatus because the inner cylinder and torsion cylinder usually are made as two separate pieces.

A disclosure of viscometer measurements including a measurement of dynamic shear of a polymer melt, is set forth in a bulletin by H. K. Bruss RheoVerfahrenstechnik GmbH. However, the viscometer discussed therein incorporates an enlarged diameter inner cylinder or "bob" and a reduced diameter torsion measuring cylinder constructed from two separate components, thus giving rise to erroneous readings as described above.

U.S. Pat. No. 3,128,620 (Gupta) also relates to a torque tube rotational viscometer, for measuring the dynamic shear of a fluid. It includes a torque sleeve mounted concentrically within a cylindrical rotor and coupled to a torque transmitting shaft. The sleeve is mounted with an end cap assembly through a protective mantle assembly. The rotor encircles the sleeve only along a portion of the length of the sleeve and, therefore, fluid is conducted first to a circular region defined between an outer body and the sleeve, and thereafter to an annular region between the rotor and the sleeve. Thus, this device is characterized by certain of the same drawbacks found in other prior art apparatus discussed above.

A viscometer similar to the "Couette-Hatschek" rotating cylinder viscometer is also disclosed in U.S. Pat. No. 2,817,231 (Barstow).

SUMMARY OF THE INVENTION

It is a principal object of the present invention to provide a torsion tube apparatus for measuring the viscosity and elasticity of a fluid, wherein certain of the drawbacks characteristic of prior art apparatus are minimized or eliminated.

More particularly, it is an object of the present invention to provide an apparatus which measures the viscosity and elasticity of a fluid by measuring its dynamic shear characteristics. The apparatus is formed with a smooth flow path to minimize remote and secondary fluid flows that can result in erroneous measurements.

It is another object of the present invention to provide such an apparatus in which fluid is caused to flow uniformly at uniform pressures through portions of the apparatus, in a manner such that dynamic shear forces are applied thereto.

It is yet another object of the present invention to provide such an apparatus in which the temperature and velocity of fluid flowing therethrough can be accurately controlled and made uniform.

It is a further object of the present invention to provide apparatus which determines the viscosity and elasticity characteristics of a fluid by torsionally displacing a torsion tube, in such a manner that vibration and thermal movement of a torsion transmitting shaft mounted in the tube are effectively cancelled.

These objects are satisfied, as disclosed in detail herein, by causing the fluid to be tested to flow through a long smooth annular space formed between an outer rotating cylinder and an inner torsion tube which is fixed at one end to a housing. The provision of such a smooth annular space gives rise to a self-cleaning effect wherein the incoming fluid pushes all of the previously introduced fluid through the testing device. Accordingly, there are no "dead" areas wherein the fluid may become resident for extended periods and thereby cause erroneous measurements. A torsion indicating shaft is mounted within the torsion tube at the free end thereof, and extends through the entire length of the tube for termination in a detecting device which senses the degree of twisting movement of the shaft. As described above with respect to the prior art, the rotational movement of the outer shaft causes a rotational movement of the fluid. However, by means of the present invention that movement of the fluid is applied directly to the surface of the torsion tube. Thus, the twisting movement of the indicating shaft results from the torsional movement at the free end of the torsion tube, caused by a torque applied to the tube by the rotational movement of the fluid passing therethrough. As an end result the viscosity and elasticity of the fluid can be calculated from various output data including the degree of twisting movement of the shaft.

More specifically, in general accordance with the present invention, the outer diameter of the torsion tube and the inner diameter of the rotating cylinder are substantially uniform along their entire lengths, thereby forming a smooth flow path for the fluid. A mechanism rotates the outer cylinder in an oscillating manner to impart the required torque to the fluid as it is caused to flow through the annular space.

In accordance with a further feature of the present invention, the housing is formed with an orifice through which the fixed end of the torsion tube projects in a concentric relation, thereby defining an annular inlet opening to the long annular flow path for the fluid. Fluid is fed through an inlet conduit communicating with the inlet opening to the flow path.

By these means, that is, due to the fact that the cylindrical stream of fluid under test is substantially uniform throughout its entire length, between the input and output ports of the viscosity testing device, no aberrations may be generated in the shear forces which are being measured. Restated, an important difference between the present invention and the prior art is that the present invention avoids any discontinuities in the cylindrical stream of fluid being tested. This is accomplished, for example, by the device illustrated in the drawings wherein the shear area of the apparatus does not embody any cross-sectional discontinuities.

With relation to still another feature of the present invention, the detecting device for sensing twisting movement of the shaft comprises a pair of opposed differential transducers coupled to the shaft in such a way as to cancel out vibratory and thermal movement of the shaft.

These and other objects, features and aspects of the present invention will be pointed out in or will be understood from the following detailed description provided below in conjunction with the accompanying drawings.

BRIEF DESCRIPTION OF THE DRAWINGS

FIG. 3 is an end view of the torsion tube apparatus shown in FIG. 2, taken from the right and illustrating the dual, opposed, differential transducers.

DETAILED DESCRIPTION OF THE PREFERRED EMBODIMENT

Figure 1:
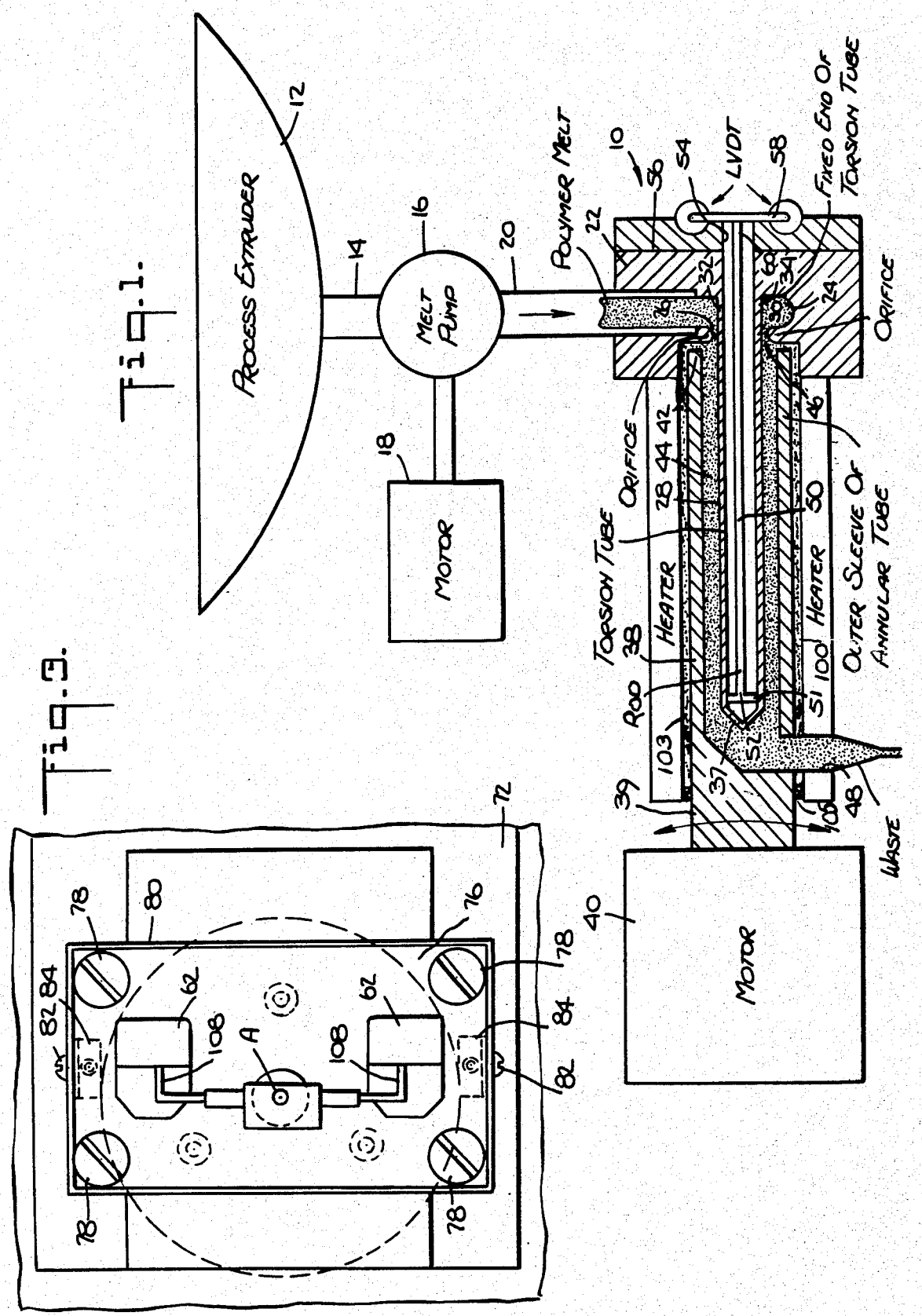
FIG. 1 is a diagrammatic, cross-sectional view of the torsion tube apparatus, in accordance with the present invention, for measuring the viscosity and elasticity of a fluid.

As diagrammatically shown in FIG. 1, the torsion tube apparatus, generally indicated at 10 and in accordance with the preferred embodiment of the present invention, is adapted to measure the elasticity and viscosity of a fluid such as a polymer melt. This apparatus may be operated in real-time and on-line and for convenience will be described and illustrated as used with a process extruder 12 that produces such a polymer melt. Of course, if desired the apparatus of the present invention may be adapted to other environments for measuring the viscosity and elasticity of other kinds of fluids.

In the embodiment described here, the process extruder 12 is connected through a conduit 14 to a melt pump 16. A motor 18 drives the melt pump to supply the polymer melt from the extruder under pressure through a fluid input duct 20 to the apparatus 10.

The apparatus 10 includes a housing 22 formed with an annular input chamber 24, communicating with the input duct 20, and a reduced diameter, circular orifice 26 opening from the chamber. The combination of the input chamber 24 and the restricting orifice 26 provides a uniform pressure around the entire periphery of the orifice. Accordingly, the flow of material is uniform as it enters the cylindrical void, and this contributes to the above-mentioned self-cleaning effect.

A hollow torsion tube 28 of substantially uniform diameter has a first fixed end 32 rigidly attached to the housing 22 at the base 34 of the input chamber 24, a portion 30 that projects from the first end concentrically through the orifice 26, and a free end 36 terminating in a conical tip 37 that projects away from the fixed end 32. The torsion tube is made as a single, integrated structure.

The apparatus 10 further includes a hollow outer cylinder 38 having substantially uniform inside and outside diameters. The cylinder is mounted at a first end 39 to the shaft of a motor 40. The motor rotates the cylinder about its axis in any desired manner including, for example, stepped, oscillatory and continuous motions as described in greater detail below. The outer cylinder projects from the motor in a coaxial, telescoping relation with and about the torsion tube 28 and terminates in a second end 42 adjacent the housing 22 in the region of the orifice 26. Therefore, the outer cylinder and torsion tube define an inner elongated annular space 44, having substantially uniform inside and outside diameters, which constitutes a smooth flow path for the polymer melt. In addition, the orifice 26 and the portion 30 of the torsion tube form an annular outlet from the chamber 24 and inlet 46 to the annular space 44 for feeding the polymer melt thereto. A radially directed discharge opening 48, communicating with the annular space, may be formed in the outer cylinder so that the polymer melt can be discharged from the apparatus as waste at the end of its flow path through the annular space.

A torsion-transmitting shaft 50 is mounted in coaxial relation within the hollow torsion tube. A tie rod 51 extends perpendicularly to the shaft 50 and is rigidly attached to one of its ends 52. The fixing element 51 diametrically spans and is fixed to the interior of the torsion tube in the region of the free end 36 of the tube. A second, projecting end 60 of the shaft extends through a bore 54 formed in the housing 22 and terminates in the region of the side 56 of the housing opposite that from which the torsion tube projects. A short coupling rod 58 is secured to the projecting end 60 of the shaft 50 and extends generally perpendicularly thereto. Dual linearly variable differential tranducers 62 are mounted on the housing, each at an equal distance from the common axis A of the shaft, to receive loads in opposite angular directions. Each end of the coupling rod is linked to a different one of the transducers to apply such a load thereto.

A cylindrical heater 64, which supplies heat to the outer cylinder 38 and to the fluid flowing through the inner annular space, is mounted in coaxial relation about the outer cylinder.

The torsion tube apparatus generally described above operates as follows. A small portion of the polymer melt is diverted from the process extruder 12 to the melt pump, which is operated by the motor 18 to supply the melt under pressure to the inlet chamber 24 of the housing. The supply of polymer melt may be continuous or intermittent. Thereafter, the polymer melt flows substantially uniformly and at substantially uniform pressure through the annular inlet opening 46 to the elongated inner annular space 44 defined between the torsion tube 28 and the outer cylinder 38. After flowing through the space 44, the melt is discharged through the discharge opening 48.

While the polymer melt is in the annular space, the outer cylinder is either oscillated or continuously rotated about its axis by the motor 40. Oscillatory movement of small amplitude, for example, plus or minus 0.5 radians at a frequency of from about 0.1 to 500 radians per second, is preferred. Rotational movement of the outer cylinder creates a shear force between the cylinder and the melt that, in turn, creates a shear force between the fluid and the torsion tube 28. The tube is torsionally displaced by an amount related to the viscosity and elasticity of the melt as a result of the shear drag on the outer surface of the tube. This displacement is transmitted through the fixing element 51 to the shaft 50, and then through the coupling rod 58 to the differential transducers 62 as forward and reverse movements. The transducers each produce an electric signal related to the loads which, with proper calibration, may be used to indicate the viscosity and elasticity of the melt.

The torsion tube apparatus of the present invention generally described above provides several important advantages over prior art apparatus. Specifically, the configuration of the orifice 26 and the portion 30 of the torsion tube 28 projecting through it, defining the annular inlet opening, promotes a substantially uniform supply of fluid at substantially uniform pressure. Also, the uniform inside and outside diameters of the annular flow space 44 provide a smooth movement which constrains the fluid to have a constant thickness at all points at which it contacts the torsion tube along the entire length of the tube. Therefore, secondary fluid currents or flows which might result in errors in viscosity and elasticity measurement are mitigated.

The use and positions of dual differential transducers 62 also effectively cancel or dampen vibration and thermal movement of the torsion-transmitting shaft in a manner described in greater detail below.

The torsion tube apparatus generally described above is shown more specifically in FIGS. 2 and 3. As can be seen there, the housing 22 is formed with a radially directed inlet conduit 66 that receives and is sealed to the input duct 20. The inlet conduit 66 terminates in the input chamber 24. A mounting socket 68 is formed at the base of the chamber 24. The torsion tube 28 has an enlarged diameter portion 70 fixed rigidly in the socket 68. An end cap 72 is mounted in fixed relation to the side 56 of the housing 22 and a gasket 74 seals the area therebetween.

The outer cylinder 38, which may be stainless steel having a copper sheath 86 for enhancing heat transmission, is linked to the drive shaft 88 of the motor 40 by a suitable rotation-transmitting coupling 90. The other end 42 of the outer cylinder 38 is supported in a bearing 92 mounted in an annular recess 94 in the housing 22, in order to maintain the coaxial relationship between the cylinder 38 and torsion tube 28.

Figure 2:
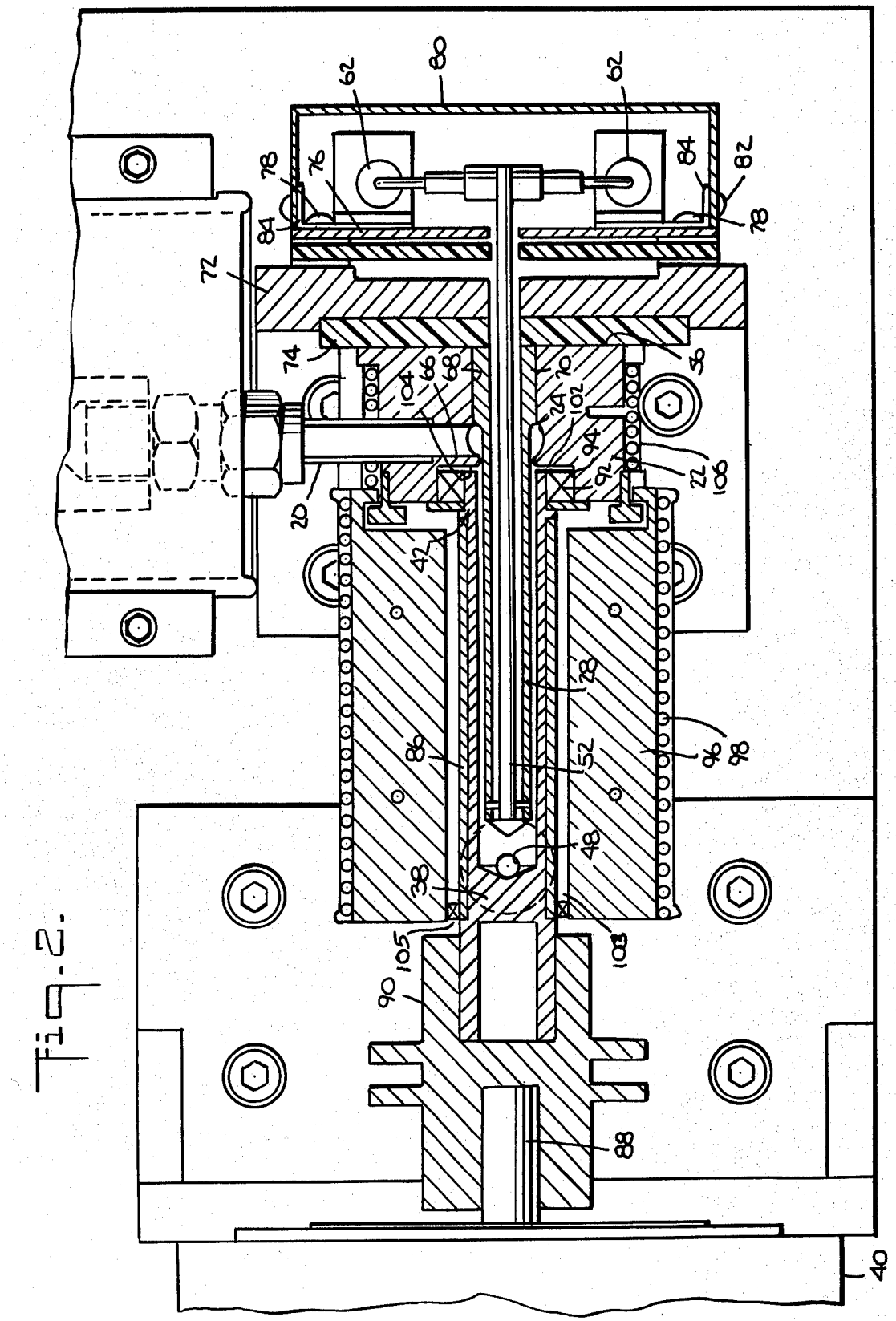
FIG. 2 is a cross-sectional view of a preferred form of the torsion tube apparatus depicted in FIG. 1.

As can be seen in FIG. 2, the heater 64 comprises a cylindrical heater block 96 and a heating coil 48 surrounding the block. An inner bore 100, of diameter slightly larger than the outside diameter of the outer cylinder, is provided in the block 96. A small gap 102 may be provided between the second end 42 of the outer cylinder and the wall 104 of the housing adjacent the orifice 26. In this regard a small amount of the polymer melt, fed under pressure through the annular inlet opening 46, may divert through the gap 102 and bleed through the antifriction bearing 92 to the outer annular space 103 between the bore 100 and the outer surface of the outer cylinder 38. At the low-pressure discharge end of the torsion tube a seal 105 is provided between the heater wall 96 and the outer sleeve 38, so that the polymer melt in the outer area 103 may be directed for discharge to the outlet 48. The polymer melt material filling this outer annular space 103 promotes conduction of heat from the heater block to the outer cylinder, and hence, to the polymer melt flowing through the inner annular space 44. This enhanced heat conduction aids in the uniform heating of the apparatus and of the fluid flowing therein. As can also be seen in FIG. 2, a secondary heating coil 106 surrounds a portion of the housing to further promote uniform heating of the apparatus.

The dual, linearly variable, differential transducers 62 are mounted on a base plate 76 which is secured to the end cap 72 by screws 78. The transducers are further enclosed by a cover 80 secured to the base plate 76 by screws 82 tapped into suitable angle members 84 fixed to the base plate. The cover protects the transducers from damage as well as from external disturbances.

As can be seen in FIG. 3, the differential transducers 62 are mounted on the base plate 76 at substantially diametrically opposed positions relative to the axis A of the shaft 52. The coupling rod 58 includes a pair of links 108, each of which extends from one extreme thereof in parallel relation to the other. Each link 108 is further coupled to one transducer 62 to transmit twisting movement of the shaft thereto. Thus, the transducers are mounted at substantially diametrically opposed locations relative to the axis A to receive parallel but angularly opposed loads. That is, when one transducer receives a forward movement of the rod 58, the other receives a reverse movement. This arrangement and mounting configuration of the transducers substantially negates vibration and thermal movement of the shaft 50 during viscosity and elasticity measurements.

The most desirable rate of fluid flow may be selected by controlling the speed of the motor-pump combination (16, 18), whereby the fluid is subjected to a continuous axial shear as it wets the surfaces of the torsion tube 28 and the outer cylinder 38. A small circumferential shear, resulting from the relatively small rotative displacement of the outer cylinder 38, is superposed on the above-described axial shear when the fluid is pumped continuously through the device. In this manner valuable dynamic test data may be obtained as a result of measurements read-out from the transducers 62. In an alternative mode of operation the pump 16 may be stopped, thus stopping the continuous flow of test material through the cylinder. Under this procedure there is no axial flow, and no axial shear, so that measurements read-out from the transducers 62 result solely from rotative shear caused by the rotatably moving outer sleeve 38.

It is apparent from the above description of the present invention that substantial advantages are provided thereby. Errors which might result from secondary fluid flow between the torsion tube and outer cylinder and elsewhere in the apparatus are eliminated. Furthermore, the polymer melt is supplied at a constant rate to the annular space between the tube and outer cylinder, thereby ensuring a uniform and self-cleaning flow of the fluid being tested.

It will also be appreciated that modifications may be made to the described structure by those skilled in the art. For example, the transducers may be mounted at diametrically opposed locations relative to the axis A, but to receive shaft movements in the same angular direction, rather than in opposed directions.

Accordingly, while a description of a preferred embodiment of the present invention has been set forth above, it is to be understood that this is for purposes of illustration. Still other modifications may be made to the described torsion tube apparatus for measuring elasticity and viscosity of fluids in order to adapt it to particular applications.

What is claimed is:

1. A torsion tube apparatus, for use in making on-line measurement of the viscosity and elasticity of a fluid comprising:
   a housing member;
   an outer cylinder projecting from and rotatably connected to said housing member;
   means for rotating said cylinder;
   an elongated torsion tube disposed concentrically within and radially spaced from said cylinder, said tube having one end fixed to said housing member and having its other end freely disposed within said cylinder for torsional movement with respect to said fixed end, and an outer surface extending axially between said one end and said other end to establish an annular void between said outer surface of the torsion tube and said cylinder;
   means for introducing a continuous flow of fluid into the interior of said cylinder at said one end of said tube and for removing the fluid from the cylinder at the other end thereof, wherein a rotating motion of the fluid, caused by rotation of said cylinder, exerts a torsional force directly on the outer surface of said torsion tube;
   a torsion-indicating shaft extending concentrically through said torsion tube and having one end fixed to said other end of said torsion tube, said shaft extending through said housing; and
   indicator means coupled to the other end of said shaft;
   wherein said torsional force on said outer surface of said torsion tube provides the sole source of rotative movement for said shaft and wherein said assembly provides a smooth axial path for the fluid which flows continuously through said annular void between said outer cylinder and said outer surface of said torsion tube.

2. A torsion tube apparatus as set forth in claim 1, further comprising a fluid input duct connected to said housing member and wherein said housing member provides an annular input chamber and a restricting orifice disposed at said one end of said tube and in communication with said input duct, said fluid being injected uniformly through said orifice into said annular void in the region of said tube.

3. A torsion tube apparatus as set forth in claims 1 or 2, wherein said indicator comprises opposed, dual, differential transducers, and wherein said opposed transducers measure the rotative movement of said shaft resulting from torsional movement of said tube, while cancelling out vibratory and thermal movement of said shaft.

4. A torsion tube apparatus for measuring the viscosity and elasticity of a fluid, said apparatus comprising:
   a housing;
   an elongated cylindrical torsion tube having substantially uniform diameter along its length, further having a fixed end mounted in non-rotative relation with said housing and a free end projecting away from said fixed end;
   an outer cylinder mounted for rotation about its axis relative to said housing and in coaxial, spaced relation around said torsion tube, said outer cylinder and said torsion tube thereby defining an inner elongated annular space having substantially uniform inside and outside diameters along its length and forming a smooth flow path for the fluid;
   means for rotating said outer cylinder;
   a torsion-transmitting shaft mounted coaxially within said torsion tube having a first end fixed thereto in the region of said free end and a second end projecting to the region of said housing;
   indicating means coupled to said second end of said shaft for indicating torsional forces therein; and
   means for introducing fluid into the inner annular space to flow smoothly therethrough while said outer cylinder is rotated by said rotating means;
   whereby rotation of said cylinder creates a rotational shear force between it and the fluid, and, in turn, between the fluid and said torsion tube to directly cause torsional force to develop at said free end of said torsion tube relative to said fixed end and to be transmitted by said shaft to said indicating means, the amount of the torsional force being related to the viscosity and elasticity of the fluid.

5. A torsion tube apparatus according to claim 4, wherein said torsion tube is formed as a single integrated member, thereby providing a self-cleaning flow path for the fluid.

6. A torsion tube apparatus according to claim 4, wherein said housing is formed with an orifice through which said torsion tube projects in concentric relation thereby to define an annular inlet opening to said inner annular space, and wherein said apparatus further comprises an inlet conduit communicating with said inlet opening for supplying fluid thereto.

7. A torsion tube apparatus according to claim 4, further comprising:
   heater means for heating fluid flowing through said annular space;
   a cylinder block, for supporting said heater means, mounted in concentric spaced relation about said outer cylinder to define an outer annular space therewith; and means for conducting fluid to said outer annular space for flow therethrough to promote transmission of heat by conduction from said cylindrical block to said outer cylinder and, in turn, to fluid flowing through said inner annular space.

8. A torsion tube apparatus according to claim 7, wherein said housing is formed with an orifice through which said torsion tube projects in concentric relation thereby to define an annular fluid inlet opening, and wherein said outer cylinder comprises a first end coupled to said rotating means and a second end projecting to the region of said inlet opening but spaced from said housing adjacent said inlet opening, said outer cylinder and said housing defining said conducting means which permits a portion of the fluid supplied to said inlet opening to flow to said outer annular space.

9. A torsion tube apparatus according to claim 4, further comprising a coupling rod fixed to said second end of said shaft and extending perpendicularly thereto, and wherein said indicating means comprises a pair of differential transducers, each of said differential transducers being mounted on said housing and coupled to said coupling rod at a location remote from said shaft.

10. A torsion tube apparatus according to claim 9, wherein said differential transducers are mounted at the same distance from and at diametrically opposed positions relative to the axis of said shaft, each of said transducers being adapted to receive tension and compression loads applied in mutually parallel directions perpendicular to said coupling rod.

11. A torsion tube apparatus according to claim 10, wherein said differential transducers are mounted respectively to receive load in opposite angular directions.

12. A torsion tube apparatus according to claim 10, wherein said differential transducers are mounted respectively to receive load in the same angular direction.

13. A torsion tube apparatus adapted for use in on-line measurement of the viscosity and elasticity of a fluid, said apparatus comprising:
a housing formed with a circular outlet orifice;
an elongated cylindrical torsion tube having substantially uniform diameter along its length, further having a fixed end mounted in non-rotative relation with said housing, a portion projecting in concentric relation through said orifice thereby to define an annular inlet opening therewith, and a free end projecting from said portion and said fixed end;
an outer cylinder mounted for rotation about its axis relative to said housing and in coaxial spaced relation around said torsion tube, said outer cylinder and said torsion tube thereby defining an inner elongated annular space having substantially uniform inside and outside diameters along its length and forming a smooth flow path for the fluid;
means for rotating said outer cylinder;
a torsion-transmitting shaft mounted coaxially within said torsion tube having one end fixed thereto in the region of said free end and a second end projecting to the region of the housing;
a pair of opposed differential transducers coupled to said shaft for indicating torsional forces therein, said transformers being mounted with said housing and coupled to said shaft so that application of a forward movement by said shaft to one results in application of a reverse movement by said shaft to the other; and
means for introducing fluid through said annular inlet opening into said annular space to flow smoothly therethrough while said outer cylinder is rotated; whereby rotation of said outer cylinder creates a rotational shear force between it and the fluid, and, in turn, between the fluid and said torsion tube to directly cause torsional force to develop at said free end of said torsion tube that is transmitted as tension and compression loads to said differential transformers, the amount of the torsional force being related to the viscosity and elasticity of the fluid.

14. A torsion tube apparatus according to claim 13, wherein said torsion tube is formed as a single, integrated member.

15. A torsion tube apparatus according to claim 13, further comprising:
heater means for heating fluid flowing through said annular space;
a cylindrical block, for supporting said heater means, mounted in concentric spaced relation about said outer cylinder to define an outer annular space therewith; and
means for conducting fluid to said outer annular space for flow therethrough to promote transmission of heat by conduction from said cylindrical block to said outer cylinder and, in turn, to fluid flowing through said inner annular space.

16. A torsion tube apparatus according to claim 15, wherein said outer cylinder comprises a first end coupled to said rotating means and a second end projecting to the region of said inlet opening but spaced from said housing adjacent said inlet opening, said outer cylinder and said housing thereby defining said conducting means which permits a portion of the fluid supplied to said inlet opening to flow to said outer annular space.

17. A torsion tube apparatus according to claim 13, further comprising a coupling rod fixed to said second end of said shaft and extending perpendicularly thereto, each of said differential transducers being mounted on said housing and coupled to said coupling rod at a location spaced from said shaft.

18. A torsion tube apparatus according to claim 17, wherein said differential transducers are mounted at the same distance from and at diametrically opposed positions relative to the axis of said shaft, each of said transducers being adapted to receive forward and reverse movement applied in mutually parallel directions perpendicular to said coupling rod.

19. A torsion tube apparatus according to claim 13, wherein said rotating means is adapted to rotate and counter rotate said cylinder in regular oscillatory fashion.

20. A torsion tube apparatus according to claim 13, wherein said outer cylinder comprises a discharge conduit for discharging fluid from said inner annular space.

* * * * *